United States Patent [19]
Li et al.

[11] Patent Number: 6,117,161
[45] Date of Patent: *Sep. 12, 2000

[54] FASTENER AND FASTENING METHOD, PARTICULARLY FOR FASTENING SUTURES TO BONE

[75] Inventors: Lehmann K. Li, Milford, Conn.; Ray Fujikawa, Cincinnati, Ohio

[73] Assignee: Li Medical Tecnologies, Inc., Shelton, Conn.

[ * ] Notice: This patent issued on a continued prosecution application filed under 37 CFR 1.53(d), and is subject to the twenty year patent term provisions of 35 U.S.C. 154(a)(2).

[21] Appl. No.: 08/470,988

[22] Filed: Jun. 6, 1995

[51] Int. Cl.⁷ ..................................................... A61B 17/04
[52] U.S. Cl. ............................................. 606/232; 623/13
[58] Field of Search ................................ 606/232, 75, 73, 606/72, 60, 69; 623/13; 24/61, 109, 114.7, 509, 90 TA

[56] References Cited

U.S. PATENT DOCUMENTS

| | | |
|---|---|---|
| Re. 34,293 | 6/1993 | Goble et al. . |
| Re. 34,762 | 10/1994 | Goble et al. . |
| 1,247,621 | 11/1917 | Bennett . |
| 2,100,570 | 11/1937 | Saleh . |
| 2,143,086 | 1/1939 | Pleister . |
| 2,213,715 | 9/1940 | Monahan .............................. 24/114.7 |
| 2,453,056 | 11/1948 | Zack . |
| 2,562,419 | 7/1951 | Ferris . |
| 3,048,177 | 8/1962 | Takaro . |
| 3,155,095 | 11/1964 | Brown . |
| 3,254,650 | 6/1966 | Collito . |
| 4,011,602 | 3/1977 | Rybicki et al. . |
| 4,233,981 | 11/1980 | Schomacher . |
| 4,293,259 | 10/1981 | Liebig . |
| 4,447,915 | 5/1984 | Weber . |
| 4,454,612 | 6/1984 | McDaniel et al. . |
| 4,501,266 | 2/1985 | McDaniel . |
| 4,708,132 | 11/1987 | Silvestrini . |
| 4,738,255 | 4/1988 | Goble et al. . |

(List continued on next page.)

FOREIGN PATENT DOCUMENTS

| | | |
|---|---|---|
| 0270704 | 6/1988 | European Pat. Off. . |
| 1368021 | 6/1964 | France . |
| 2622430 | 5/1989 | France . |
| 343992 | 3/1931 | United Kingdom . |
| WO/92/04874 | 4/1992 | WIPO . |

*Primary Examiner*—Michael Buiz
*Assistant Examiner*—Lien Ngo
*Attorney, Agent, or Firm*—Ostrolenk, Faber, Gerb & Soffen, LLP

[57] ABSTRACT

A fastener comprising a longitudinally extending member having a hub region and at least two arms extending in a longitudinal direction from the hub region, the member defining a plane and having a length and a width less than the length, the arms each being provided with a sharp edge, the hub region being provided with an engaging member for receiving a rotational force about an axis perpendicular to the plane of the member for rotating the member in the plane of the member, the fastener adapted to be inserted in a longitudinally extending groove in an object to which the fastener is to be secured, the groove being at least coextensive with the length of the longitudinally extending member and having a width at least as large as the width of the member, the fastener being adapted to be rotated via the rotational force once inserted in the groove so that the sharp edges of the arms cut into sides of the grooves thereby forming undercuts securing the fastener in the object.

41 Claims, 5 Drawing Sheets

U.S. PATENT DOCUMENTS

| | | | |
|---|---|---|---|
| 4,741,330 | 5/1988 | Hayhurst | 606/148 |
| 4,744,793 | 5/1988 | Parr et al. . | |
| 4,747,407 | 5/1988 | Liu et al. . | |
| 4,759,765 | 7/1988 | Van Kampen . | |
| 4,772,286 | 9/1988 | Goble et al. . | |
| 4,776,330 | 10/1988 | Chapman et al. . | |
| 4,870,957 | 10/1989 | Goble et al. . | |
| 4,875,474 | 10/1989 | Border . | |
| 4,892,547 | 1/1990 | Brown . | |
| 4,898,156 | 2/1990 | Gatturna et al. | 606/72 |
| 4,899,743 | 2/1990 | Nicholson et al. . | |
| 4,901,711 | 2/1990 | Goble et al. . | |
| 4,911,153 | 3/1990 | Border . | |
| 4,927,421 | 5/1990 | Goble et al. . | |
| 4,946,468 | 8/1990 | Li . | |
| 4,959,071 | 9/1990 | Brown et al. . | |
| 4,960,420 | 10/1990 | Goble et al. . | |
| 4,968,315 | 11/1990 | Gatturna . | |
| 4,985,032 | 1/1991 | Goble . | |
| 4,986,263 | 1/1991 | Dickerson et al. . | |
| 4,997,433 | 3/1991 | Goble et al. . | |
| 5,002,550 | 3/1991 | Li . | |
| 5,002,574 | 3/1991 | May et al. | 623/13 |
| 5,011,473 | 4/1991 | Gatturna . | |
| 5,013,316 | 5/1991 | Goble et al. . | |
| 5,019,105 | 5/1991 | Wiley . | |
| 5,037,422 | 8/1991 | Hayhurst et al. . | |
| 5,037,426 | 8/1991 | Goble et al. . | |
| 5,046,513 | 9/1991 | Gatturna . | |
| 5,078,730 | 1/1992 | Li . | |
| 5,084,058 | 1/1992 | Li . | |
| 5,087,263 | 2/1992 | Li . | |
| 5,092,891 | 3/1992 | Kummer et al. . | |
| 5,094,563 | 3/1992 | Carletti . | |
| 5,129,902 | 7/1992 | Goble et al. . | |
| 5,133,723 | 7/1992 | Li et al. . | |
| 5,141,520 | 8/1992 | Goble et al. . | |
| 5,147,362 | 9/1992 | Goble . | |
| 5,152,764 | 10/1992 | Goble . | |
| 5,161,916 | 11/1992 | White et al. . | |
| 5,174,087 | 12/1992 | Bruno . | |
| 5,176,682 | 1/1993 | Chow . | |
| 5,192,303 | 3/1993 | Gatturna et al. . | |
| 5,203,787 | 4/1993 | Noblitt et al. . | |
| 5,207,679 | 5/1993 | Li . | |
| 5,250,058 | 10/1993 | Miller et al. . | |
| 5,263,991 | 11/1993 | Wiley et al. . | |
| 5,266,075 | 11/1993 | Clark et al. . | |
| 5,268,001 | 12/1993 | Nicholson et al. . | |
| 5,300,077 | 4/1994 | Howell . | |
| 5,306,290 | 4/1994 | Martins et al. . | |
| 5,312,416 | 5/1994 | Spaeth et al. . | |
| 5,312,422 | 5/1994 | Trott . | |
| 5,312,438 | 5/1994 | Johnson . | |
| 5,313,962 | 5/1994 | Obenchain . | |
| 5,314,427 | 5/1994 | Goble et al. . | |
| 5,314,429 | 5/1994 | Goble . | |
| 5,314,433 | 5/1994 | Li . | |
| 5,318,577 | 6/1994 | Li . | |
| 5,324,308 | 6/1994 | Pierce . | |
| 5,330,534 | 7/1994 | Herrington et al. . | |
| 5,342,366 | 8/1994 | Whiteside et al. . | |
| 5,350,380 | 9/1994 | Goble et al. . | |
| 5,354,298 | 10/1994 | Lee et al. . | |
| 5,354,300 | 10/1994 | Goble et al. . | |
| 5,356,413 | 10/1994 | Martins et al. . | |
| 5,358,511 | 10/1994 | Gatturna et al. . | |
| 5,372,599 | 12/1994 | Martins . | |
| 5,372,604 | 12/1994 | Trott | 606/232 |
| 5,376,120 | 12/1994 | Sarver et al. . | |
| 5,393,302 | 2/1995 | Clark et al. . | |
| 5,443,482 | 8/1995 | Stone et al. . | |
| 5,464,425 | 11/1995 | Skiba | 606/232 |
| 5,464,427 | 11/1995 | Curtis et al. . | |
| 5,486,197 | 1/1996 | Le et al. . | |
| 5,531,792 | 7/1996 | Huene . | |
| 5,545,180 | 8/1996 | Le et al. . | |
| 5,569,303 | 10/1996 | Johnson | 606/232 |

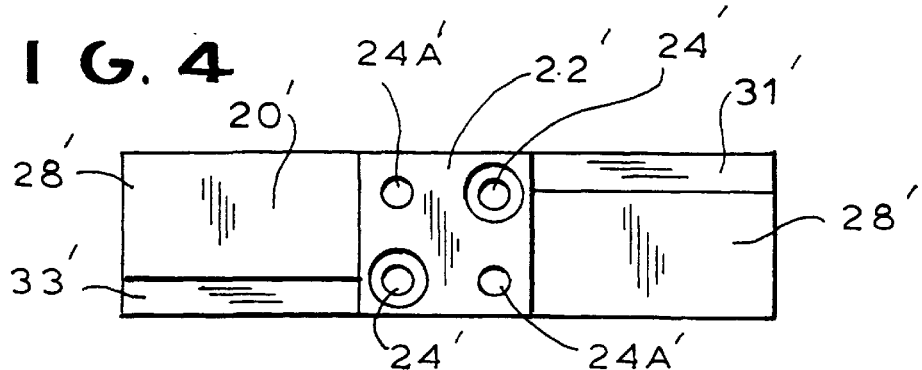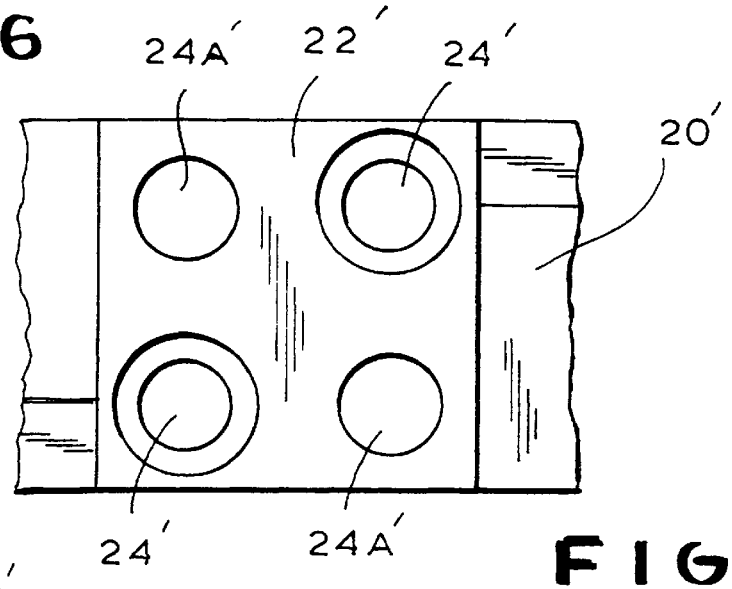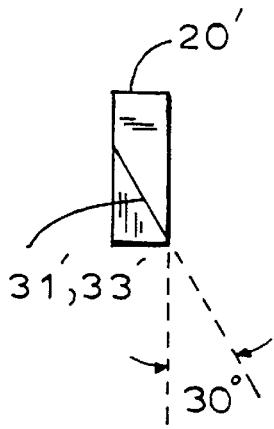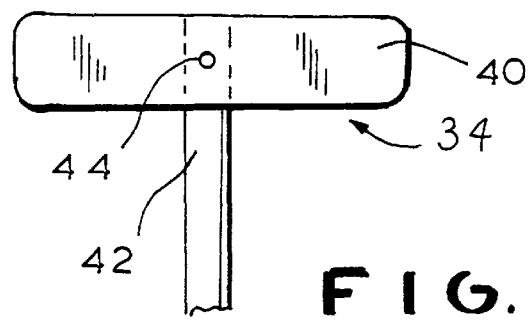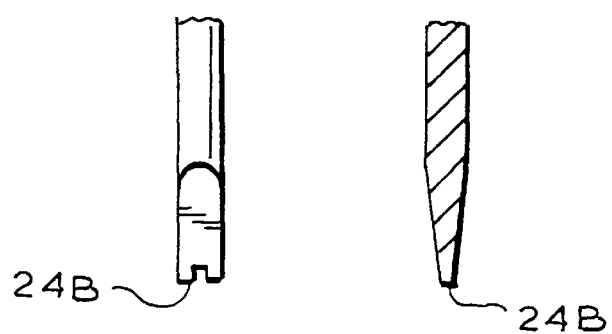

FASTENER AND FASTENING METHOD, PARTICULARLY FOR FASTENING SUTURES TO BONE

BACKGROUND OF THE INVENTION

The present invention relates to fasteners or anchors, and particularly, to fasteners or anchors for securement into medical tissue, particularly bone. The present invention finds particular application in the securement of sutures to bone, particularly for the attachment of torn ligaments or ligament replacements to bone. Although finding particular application in the medical area, the present invention is not limited thereto, and can be applied in other fields, for example, in the construction and general fastener industries.

Various suture anchors and methods of anchoring sutures in body tissue, for example, bone, are known. For example, Hayhurst et al. (U.S. Pat. Nos. 4,041,129 and 5,269,809) disclose a suture anchor having a pivotable toggle end, which upon insertion, is rotated so as to be transverse with respect to an insertion tool. The sutures then extend from the anchor through the aperture provided for the insertion tool. This anchor appears to be difficult to insert, and requires the surgical drilling of two holes, one transverse to the other hole in order to secure the anchor in, for example, hard tissue such as bone. The anchor of these references essentially forms a toggle.

U.S. Pat. Nos. 4,575,295 and 3,053,355 show two fasteners which are secured in premanufactured locking channels by a twisting action. In U.S. Pat. No. 4,575,295, the fasteners are twisted so that tabs of the fasteners underlie flanges of the premanufactured channels. The fastener has grooves therein which lock into downwardly depending tabs of the flanges of the channel. A spring biases the fastener to secure the fastener in the channel.

In U.S. Pat. No. 3,053,355, a curved nut is provided which is inserted into a channel and then twisted. The curved nut has edges which bite into the channel flanges with the edges underlying the flanges of the channel. A bolt is then inserted into the nut to secure another member to the channel.

U.S. Pat. No. 1,091,674 shows a screw fastener which has a blade which is rotated out of the longitudinal direction of the screw once the screw is inserted into a bore to fasten the screw securely into the bore. The blade rotates about an axis perpendicular to the axis of the screw.

U.S. Pat. Nos. 2,077,804 and 2,685,877 show various medical fasteners. In U.S. Pat. No. 2,077,804, the fastener includes two flat transverse members which rotate on an axis perpendicular to the longitudinal direction of the fastener thereby to secure the fastener in position.

U.S. Pat. No. 2,685,877 shows a femoral head prosthesis including two locking keys which individually pivot about an axis perpendicular to the longitudinal axis of the fastener to secure the femoral head prosthesis in position in the femur.

U.S. Pat. Nos. 5,203,787, 5,306,301, 5,403,348 and 4,741,320 show other suture anchors. U.S. Pat. No. 1,269,912 shows another general use clamping bolt.

The prior art thus shows various toggle type anchors or fasteners which are adapted to be received in undercuts or below flanges, and which prevent the anchor, through a toggle of the transverse portion of the anchor, from being pulled out of the bore in which it is disposed.

These various fasteners, whether for the construction industry or the medical field, all suffer from complications, including difficulty of use, the need to cut a transverse hole or undercut perpendicular to the direction of the insertion hole and a lack of adequate securement against forces tending to pull the fasteners out of the bores in which they are disposed. In the case of U.S. Pat. Nos. 2,077,804, 2,685,877 and 1,091,674, these patents all suffer from complications in use due to the need to rotate the securement member about axes perpendicular to the fastener axis.

A particular application in the medical field where there is a need for an improved suture anchor is in the securement of ligaments or ligament replacements to bone, and in particular, the rotator cuff ligaments i.e., the ligaments holding the humerus to the clavicle.

SUMMARY OF THE INVENTION

It is, accordingly, an object of the present invention to provide a fastener for securement into bone.

It is yet still a further object of the present invention to provide a suture anchor which can be secured in bone.

It is yet still another object of the present invention to provide a fastener which is suitable and can be adapted for use in the construction industry or in the general fastener industry, for example, for securement into wood or plastic.

It is yet still a further object of the present invention to provide a suture anchor for securement into bone which can be used to secure ligaments or ligament replacements to sutures tied to the anchor.

It is yet still a further object of the present invention to provide an anchor which is adapted to be inserted into a longitudinally extending recess and through rotation in the plane of the anchor, secured into the recess.

It is yet still a further object of the present invention to provide an anchor which can be secured into recesses of any depth, including relatively shallow recesses in bone or other members.

The above and other objects of the present invention are achieved by a fastener comprising: a longitudinally extending member having a hub region and at least two arms extending in a longitudinal direction from the hub region, the longitudinally extending member defining a plane and having a length and a width less than the length, the arms each being provided with a sharp edge; the hub region being provided with an engaging member for receiving a rotational force about an axis perpendicular to the plane of the member for rotating the longitudinally extending member in the plane of the member; the fastener adapted to be inserted in a longitudinally extending groove in an object to which the fastener is to be secured, the groove being at least coextensive with the length of the longitudinally extending member and having a width at least as large as the width of the member, the fastener being adapted to be rotated via the rotational force once inserted in the groove so that the sharpened edges of the arms cut into sides of the grooves thereby forming undercuts securing the fastener in the object.

The above and other objects of the invention are also achieved by a method for inserting a fastener in an object, the fastener having a length and a width less than the length and defining a plane, the method comprising inserting a fastener in an object, the fastener having a length and a width less than the length and defining a plane, the method comprising forming a longitudinally extending groove in the object, the groove having a longitudinal extent at least as long as the length of the fastener and having a width at least as large as the width of the fastener and less than the length of the fastener; inserting the fastener into the groove with its length along the longitudinal extent of the groove; and rotating the fastener in the plane about an axis perpendicular to the plane so that sharp edges thereof cut into sides of the groove in the object to form undercuts in the object thereby securing the fastener in the object.

The above and other objects are further achieved by a fastener comprising a longitudinally extending member having a hub region and at least two arms extending in a longitudinal direction from the hub region, the member defining a plane and having a length and width less than the length; the arms each being provided with a sharp edge; the hub region being provided with an engaging member for receiving a rotational force applied by an insertion tool having an axis, the axis of the insertion tool being perpendicular to the plane of the member, the insertion tool being provided for releasably holding the member and for rotating the member in the plane of the member about the axis; the fastener adapted to be inserted in a longitudinally extending groove in an object to which the fastener is to be secured, the groove being at least coextensive with the length of the longitudinally extending member and having a width at least as large as the width of the member, the fastener being adapted to be rotated via the rotational force once inserted in the groove so that the sharp edges of the arms cut into sides of the grooves thereby forming undercuts securing the fastener in the object.

Other objects, features and advantages of the present invention will become apparent from the detailed description which follows.

BRIEF DESCRIPTION OF THE DRAWINGS

The invention will now be described in greater detail in the following detailed description with reference to the drawings in which:

FIG. 4 shows an alternative embodiment of the anchor according to the present invention;

FIG. 5 is a side view of the anchor of FIG. 4 according to the present invention;

FIG. 6 is a top view of a portion of the anchor of FIGS. 4 and 5;

FIG. 7A shows an insertion tool for inserting anchors according to the invention;

FIG. 7B shows a portion of the insertion tool of FIG. 7a in side view;

DETAILED DESCRIPTION

Figure 1:
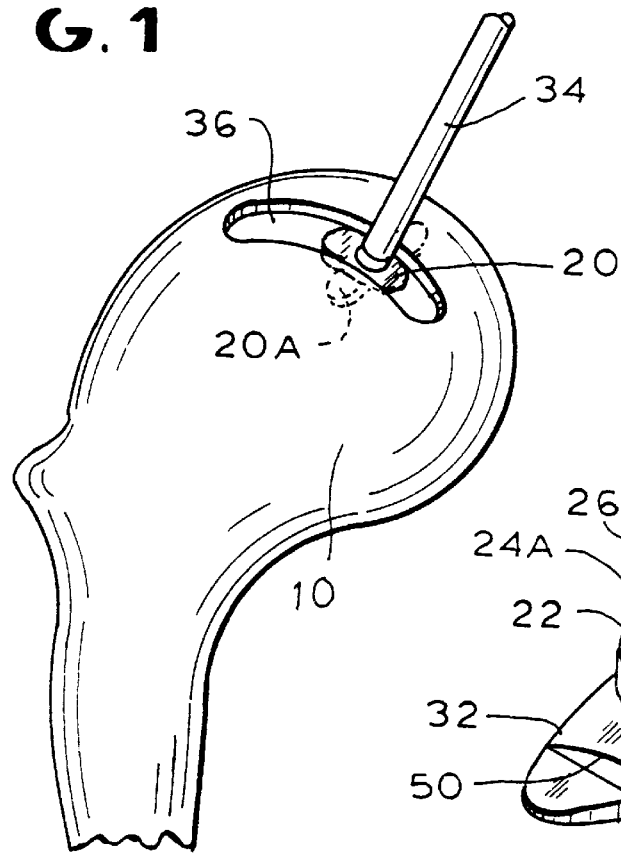
FIG. 1 shows, in perspective view, the outline of a human bone, for example, the humerus or upper arm bone, having a longitudinal recess formed therein into which the anchor of the present invention is inserted for securement.

With reference now to the drawings, FIG. 1 shows an exemplary application of the present invention. In FIG. 1, the upper portion of the humerus or upper arm bone 10 is shown. The humerus 10 is joined to the clavicle or shoulder blade by a ligament assembly known as the rotator cuff. The rotator cuff ligaments are sometimes torn away from the humerus 10, and there is a need to reattach the rotator cuff ligaments to the humerus 10 or attach a prosthetic ligament replacement.

The present invention provides a suture anchor for allowing the suturing of the torn ligaments to the bone 10. The present invention is not limited to the rotator cuff ligaments and can be employed with many other ligaments of the human body. Furthermore, the anchor of the present invention is not limited to the humerus but may be employed on other bones of the human or animal body. In addition, the invention has other uses outside the medical field as a fastener.

Figure 3A:
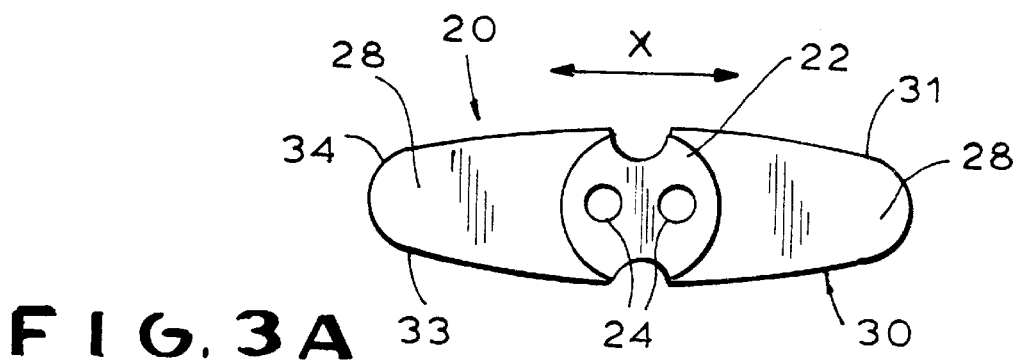
FIG. 3A is a top view of the anchor shown in FIGS. 1 and 2.

As shown in the drawing figures, the invention, in one embodiment, comprises an anchor or fastener 20 having a generally flattened oral shape in plan view, which has a longitudinal extent in the direction indicated by the arrows X in FIG. 3A. The anchor includes a hub 22 which is provided with openings 24 through which sutures 26 may be looped or fastened. Alternatively, the hub can include other attachment means, such as a screwhole, threaded shaft, rod, etc. The anchor further includes arm portions 28 which extend in the longitudinal direction. These arm portions 28 are provided with sharpened edges 30 and 32 on opposite sides thereof. The sharpened edges are adapted to cut into the object into which the fastener is implanted, e.g. if bone, the softer cancellous bone underlying the outer, harder cortical layer of bone. When the anchor 20 is twisted in the plane of the anchor by a suitable insertion device 34, to be described in detail later, the sharp edges of the arms cut into the object as it rotates, thus forming undercuts and securing the fastener in the object.

Figure 2:
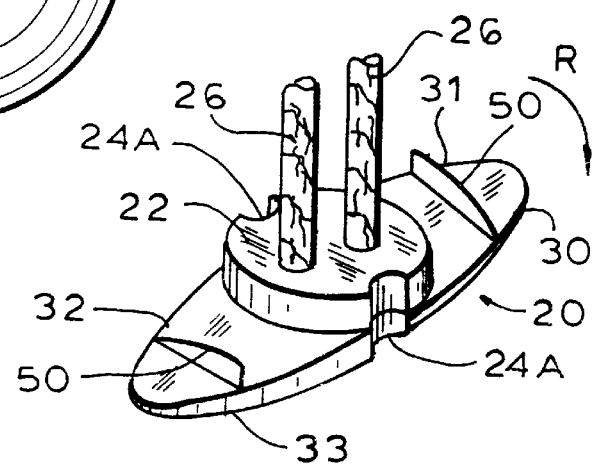
FIG. 2 shows, in perspective view, the anchor according to the present invention with sutures extending therefrom.

In use to reattach ligaments or attach ligament replacements, after an incision is made at the point where reattachment is to occur, a groove 36 having a longitudinal extent, as shown in FIG. 1, is made in the bone by any suitable means, for example, by drilling, scraping, sawing etc., as is well known in the art. The fastener 20 is then inserted into the groove with its longitudinal extent in the longitudinal direction of the groove. Groove 36 should have a longitudinal extent at least as long as the length of the fastener 20 and a width at least as wide as the fastener 20. Thereafter, the insertion tool 34 is twisted in a direction so that the sharpened edges 30 and 32 cut into and form an undercut in the cancellous bone, thereby locking the anchor 20 in the position shown in phantom in FIG. 1 at 20A. The sutures 26 are thereby secured into the bone, and the torn ligaments may be sutured to the anchor. If additional fasteners 20 are necessary, they may be inserted into the longitudinally extending groove 36 so that a plurality of the anchors may be fastened to the bone. The groove 36 accordingly should be of an extent to accommodate the number of required fasteners 20, taking into consideration the spacing required between the sutures to allow for rotation. In FIG. 2, the rotation which will secure the fastener 20 in the bone is shown by the curved arrow R.

Figure 3B:
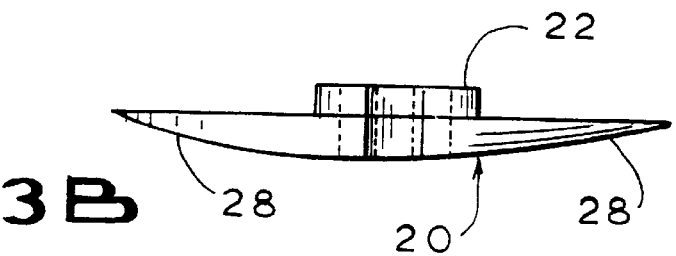
FIG. 3B is a side view of the anchor shown in FIG. 3A.

The fastener 20, as shown in FIG. 3B, may also be formed such that it has sharpened edges on all sides 30, 31, 32 and 33, so that it can be rotated in either direction, clockwise or counter-clockwise, to secure it in the groove 36 in the undercut formed in the bone.

In the embodiments shown in FIGS. 1, 2, 3A and 3B, the hub region 22 includes two side slots 24A. These slots 24A are provided so that an insertion tool 34, of the type shown generally in FIGS. 7A and 7B, for example, having spanner type protrusions 24B, will be received in the slots 24A to allow the fastener 20 to be rotated.

FIGS. 4, 5 and 6 show an alternative embodiment of the fastener according to the present invention. In the embodiment of FIG. 4, the fastener 20' has a generally rectangular shape. It has a hub region 22' having four openings, two openings 24' and two openings 24A'. The openings 24' are analogous to the openings 24 of the embodiment of FIGS. 1–3B. The sutures are looped through these openings or otherwise tied off in these openings. The openings 24A' receive the tips 24B of an insertion tool, shown generally in FIGS. 7A and 7B, thereby allowing rotation of the fastener 20' to secure it in the bone. The fastener of FIGS. 4, 5 and 6 is secured in the same way as the fastener of FIGS. 1–3B. The longitudinally extending arms 28' include two opposed sharp knife edges 31 and 33, which, as shown in FIG. 5, may be formed with an angular cutting surface inclined at 30° from the plane of the fastener.

As shown in FIG. 6 in detail, the openings 24, 24' may be formed with a 45° chamber or countersunk upper surface, thereby to prevent damage to the sutures and to facilitate insertion of the sutures into the openings 24, 24'.

FIGS. 7A and 7B show an exemplary insertion tool 34. The insertion tool may be formed in the shape of a T-shaped tool generally designated 34 having a handle 40 and extending shaft 42. The handle 40 may be suitably attached to the shaft 42 by pin 44. At the distal end, the shaft 42 includes two spanner projections 24B, shown in side view in FIG. 7B. Although a spanner type insertion tool is shown in FIGS. 7A and 7B, other insertion devices could also be employed, for example, various wrenches, screw drivers, etc. having variously shaped ends adapted to suitable corresponding engaging points of the fastener 20, 20'.

Figure 8:
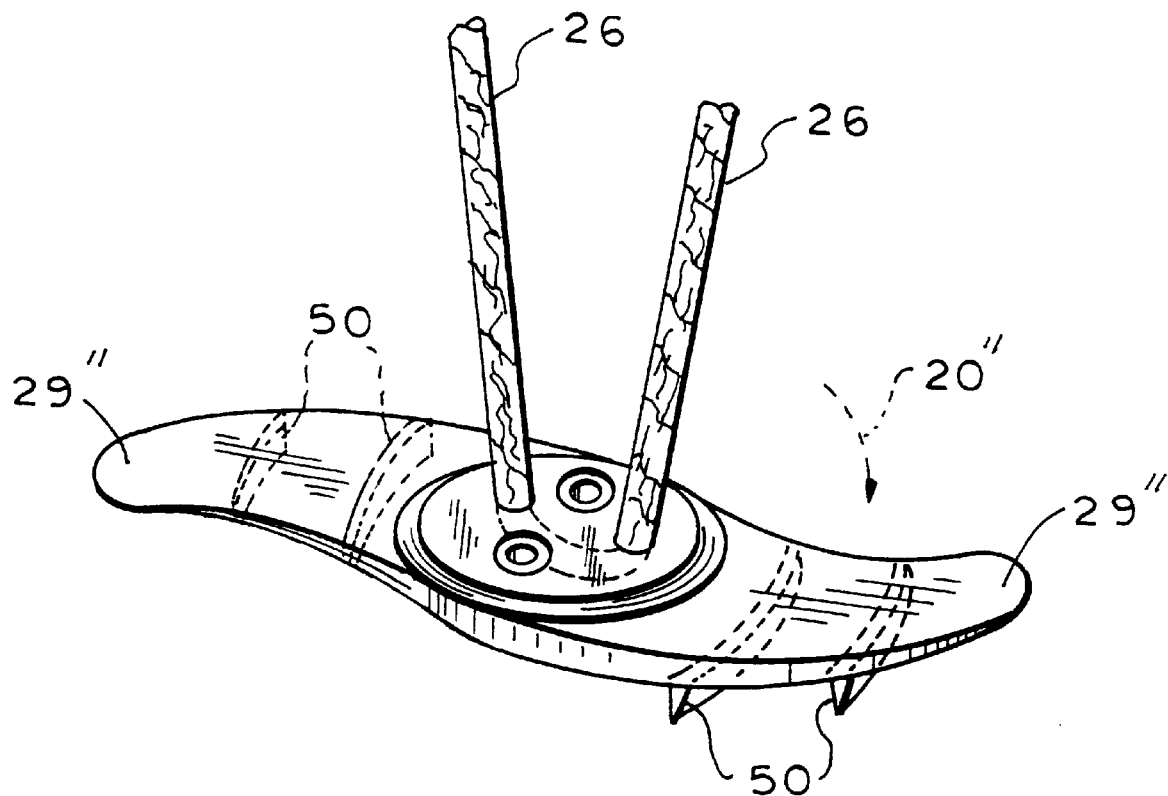
FIG. 8 shows another embodiment in perspective view of the anchor according to the present invention with sutures extending therefrom.

FIGS. 8–12 show additional embodiments of the present invention. FIG. 8 shows an embodiment 20" having sharp blade edges 30" and 32". The fastener 20" has a somewhat cyclonic shape in plan view and is formed with longitudinally extending arms 28" formed with curved tips 29" adapted to turn in a specified direction, in the embodiment shown, in the clockwise direction shown by curved arrow R". As in the embodiments shown previously, this embodiment includes 4 openings in the hub 22", two of which (24") are provided for fastening the sutures and the other two of which (24A") are adapted to receive the prongs 24B of the insertion tool, shown generally in FIGS. 7A and 7B.

Figure 9:
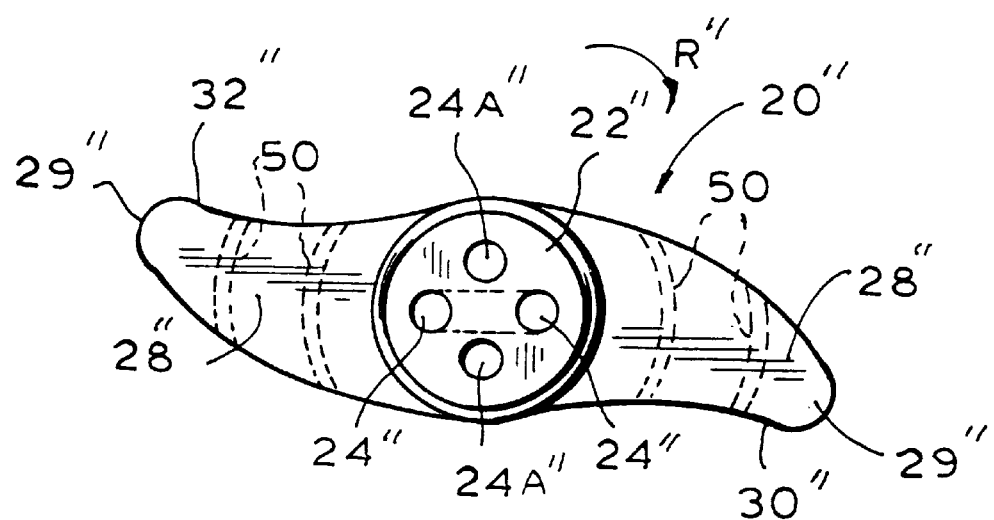
FIG. 9 shows the anchor of FIG. 8 in a bottom view.
Figure 11:
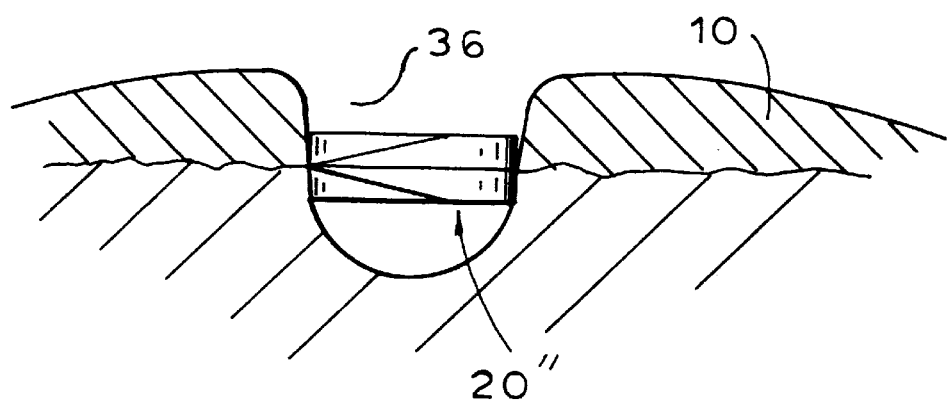
FIG. 11 shows the anchor of FIG. 10 in a side view disposed longitudinally in a longitudinally extending recess in bone prior to rotation of the anchor to secure it in the recess.

FIG. 11 shows the embodiment of FIGS. 8 and 9 inserted into a groove 36 in bone 10, prior to rotation of the anchor to cut into the bone and thus form an undercut in the bone to secure the anchor.

Figure 12:
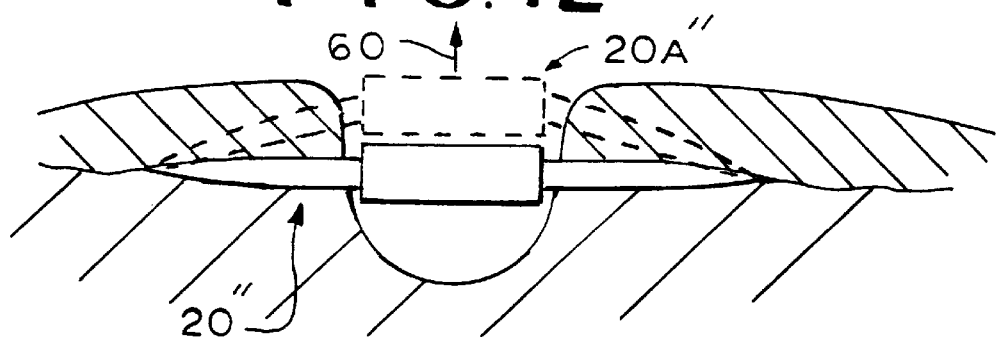
FIG. 12 schematically shows the anchor of the various embodiments implanted in bone and shows it being subjected to a force tending to pull the anchor out of the recess.

According to the embodiments shown in FIGS. 8 and 9, the fastener 20, 20' is preferably provided with at least one, and preferably a plurality of ribs or fins 50, also having sharp pointed edges as shown in the embodiment illustrated, pointing downwardly and approximately perpendicularly from the substantially planar surfaces of the fastener. These fins and ribs are suitably shaped so as to cut into the bone or other object upon rotation of the fastener. These ribs or fins are provided to prevent the anchor from being pulled out of the bone when secured in the bone by forces tending to pull the fastener outwardly. These forces are shown generally by the arrow 60 of FIG. 12. As shown in FIG. 12, a fastener 20" provided without the fins or ribs 50 is more likely to be pulled out of the bone by forces exerted in the direction 60. The reason for this is that the fastener 20" will tend to deflect or curve as shown in phantom in FIG. 12 at 20A" due to the effect of the forces 60.

Figure 13:
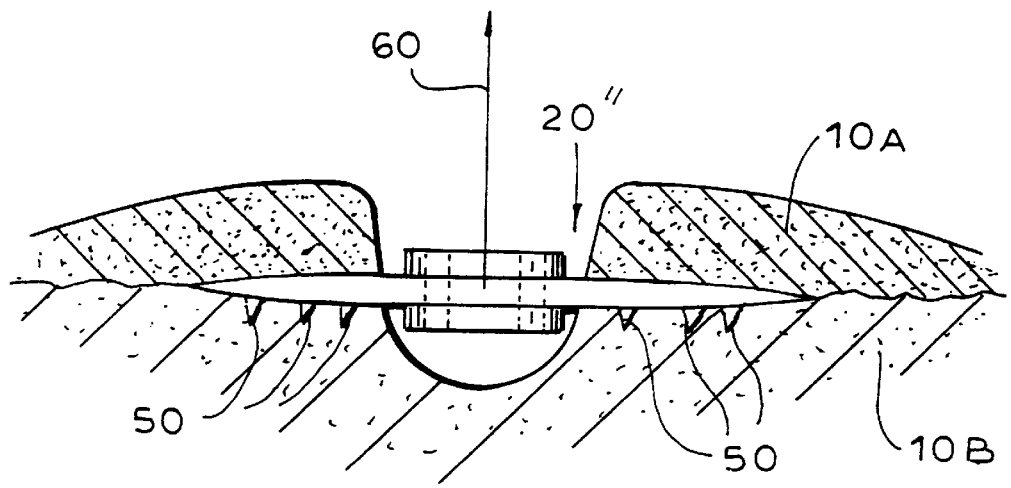
FIG. 13 schematically shows the anchor of the various embodiments, and further showing fins or ribs provided on a surface of the anchor to increase the resistance of the anchor to being pulled out of the recess.

In order to minimize the tendency of the fastener 20" to pull out of the bone, fins 50 are provided which also cut into the bone downwardly when the fastener 20" is rotated to form the undercut in the bone. As will be readily appreciated, as shown in FIG. 13, if a force 60 shown by the upwardly directed arrow is applied to the fastener, the additional lateral forces created by the fins or ribs 50, will tend to prevent the anchor from pulling out of its undercut. Although the fins or ribs 50 are shown on the bottom side of the fastener, they can also be provided on the top side, depending on the particular application. Furthermore, in order to assist in implantation of the fastener, the fins or ribs 50 may be formed so as to have a curved outline curving in the direction of the rotation applied to the fastener, as shown in FIG. 8.

Figure 10:
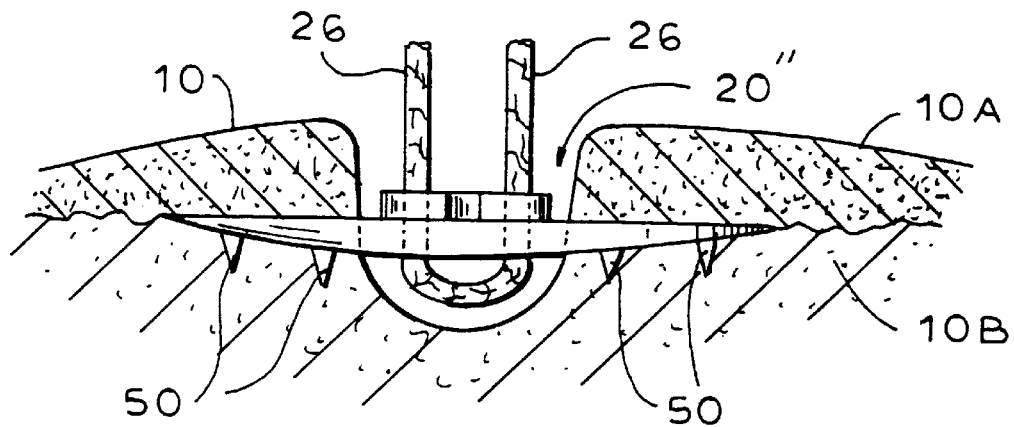
FIG. 10 shows the anchor of FIGS. 8 and 9 implanted in bone.

FIG. 10 shows the anchor 20" with the ribs 50 in place in bone 10. As shown, the bone 10 includes an upper cortical layer 10A and a lower softer cancellous layer 10B, into which the fastener is implanted.

Figure 14A:
FIGS. 14A, 14B and 14C are plan views schematically showing other forms of the anchor according to the invention.
Figure 14B:
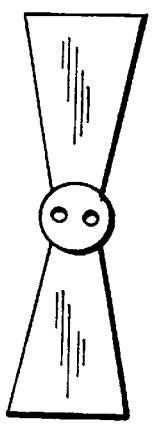
Figure 14C:

FIGS. 14, 15 and 16 show schematically and plan views, other shapes the fastener 20, 20', 20" can take. As shown in FIG. 14A, the fastener may take the shape of a propeller in plan view or have an hour glass shape as shown in FIG. 14B or the shape shown in FIG. 14C. Other shapes are equally possible as would be clear to those of skill in the art and depend upon the particular application.

Further, any of the embodiments shown can have fins or ribs 50. These are shown, for example, also in the embodiment of FIG. 2.

If the invention is used in medical applications, the materials from which the invention are preferably made include implantable metallic alloys, e.g., stainless steel and titanium, polymers, e.g., nylon or other implantable biocompatible plastics. The materials may be absorbable or resorbable. The invention may also be made of a ceramic material. If the invention is used in other applications, e.g., as a non-medical fastener, it can be made of any suitable material.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A combination comprising an insertion tool and a fastener adapted to be installed by the insertion tool, the insertion tool having an insertion tool axis, the fastener comprising:

a longitudinally extending member having a hub region and at least two arms extending in a longitudinal direction from the hub region, the longitudinally extending member defining a plane and having a length and a width less than the length, the hub region defining an axis of rotation of the longitudinally extending member which is along the insertion tool axis;

the arms each being provided with a sharp edge;

the hub region being provided with an engaging member, the engaging member being adapted to engage the insertion tool such that the plane defined by the longitudinally extending member is perpendicular to the insertion tool axis, the engaging member being adapted to receive torsional force about said insertion tool axis perpendicular to the plane of the longitudinally extending member for rotating the longitudinally extending member in the plane of the longitudinally extending member;

the fastener being adapted to be inserted in a longitudinally extending groove in an object to which the fastener is to be secured, the groove being at least coextensive with the length of the longitudinally extending member and having a width at least as large as the width of the longitudinally extending member, the fastener being adapted to be rotated via the torsional force from the insertion tool once inserted in the groove so that the sharp edges of the arms cut into sides of the grooves thereby forming undercuts securing the fastener in the object, and the insertion tool comprising a shaft extending along the insertion tool axis, the shaft having a keyed end for engaging with a mating keyed portion of the engaging member of the hub region of the fastener for providing the torsional force.

2. The fastener of claim 1, wherein the hub region includes at least one securement point for securing a suture thereto.

3. The fastener of claim 1, wherein the engaging member comprises at least one location adapted to receive an insertion tool for providing said rotational force.

4. The fastener of claim 2, wherein there are at least two securement points for securing a suture.

5. The fastener of claim 4, wherein the securement points comprise openings in the hub through which the suture traverses.

6. The fastener of claim 3, wherein the engaging member comprises at least one opening adapted to receive a portion of the insertion tool.

7. The fastener of claim 1, wherein the longitudinally extending member has the shape of a flattened oval in plan view.

8. The fastener of claim 1, wherein the sharp edges have an angle from the plane of the longitudinally extending member of about 30°.

9. The fastener of claim 1, wherein each arm has two sharp edges, thereby allowing rotation to secure the fastener in two opposite rotational directions.

10. The fastener of claim 1, further comprising at least one fin or rib projecting from a surface of each arm, the fins or ribs having sharp edges.

11. The fastener of claim 10, wherein the fins or ribs project substantially perpendicularly from the surface.

12. The fastener of claim 10, wherein the fins or ribs are curved in t he direction of the rotational force.

13. The fastener of claim 10, wherein the fins or ribs are disposed on a lower surface of the arms.

14. The fastener of claim 10, further comprising an insertion tool for releasably holding the fastener and providing the rotational force to secure the fastener.

15. The fastener of claim 1, wherein the fastener comprises a biocompatible material adapted to be inserted in bone.

16. The fastener of claim 2, wherein the fastener comprises a biocompatible material adapted to be inserted in bone and the suture is adapted to secure a ligament or ligament replacement to the bone.

17. The fastener of claim 15, wherein the member comprises one of a biocompatible metal, plastic or ceramic.

18. A method for inserting a fastener in an object with an insertion tool having an insertion tool axis, the fastener having a length and a width less than the length and defining a plane, the plane being perpendicular to the insertion tool axis, the method comprising:

forming a longitudinally extending groove in the object, the groove having a longitudinal extent which extends in a direction along a surface of the object, the longitudinal extent being at least as long as the length of the fastener and having a width at least as large as the width of the fastener and less than the length of the fastener;

inserting the fastener into the groove with its length along the longitudinal extent of the groove and substantially parallel to the surface of the object; and rotating the fastener in the plane about said axis of the insertion tool in response to a torsional force applied to the fastener from the insertion tool so that sharp edges thereof cut into sides of the groove in the object to form undercuts in the object thereby securing the fastener in the object.

19. The method of claim 18, wherein the object is bone and further comprising:

fastening a suture to the fastener, thereby to secure the suture to the bone.

20. The method of claim 18, further comprising providing fins or ribs extending from surfaces of the fastener which cut into the object when the fastener is rotated thereby to reduce the possibility of pulling the fastener out of the object to which it is secured.

21. The method of claim 18, further comprising the step of providing a fastener insertion tool for releasably holding the fastener and for performing the step of rotating the fastener to secure the fastener in the object.

22. The method of claim 19, further comprising the step of securing a ligament or ligament replacement to the suture.

23. The method of claim 18, wherein the object comprises bone tissue and the step of forming a groove comprises forming a groove in bone tissue.

24. A fastener and insertion tool for the fastener comprising:

a longitudinally extending member having a hub region and at least two arms extending in a longitudinal direction from the hub region, the longitudinally extending member defining a plane and having a length and a width less than the length;

the arms each being provided with a sharp edge;

the hub region being provided with an engaging member, the engaging member being adapted to receive a torsional force from the insertion tool, the insertion tool having an insertion tool axis perpendicular to the plane of the longitudinally extending member, the longitudinally extending member being adapted to be releasably held by the insertion tool and rotated by the insertion tool about the insertion tool axis in the plane of the longitudinally extending member, the hub region defining an axis of rotation of the longitudinally extending member which is along the insertion tool axis;

the fastener adapted to be inserted in a longitudinally extending groove in an object to which the fastener is to be secured, the groove being at least coextensive with the length of the longitudinally extending member and having a width at least as large as the width of the longitudinally extending member, the fastener being adapted to be rotated via the torsional force from the insertion tool once inserted in the groove so that the sharp edges of the arms cut into sides of the grooves thereby forming undercuts securing the fastener in the object, and the insertion tool comprising a shaft extending along the insertion tool axis, the shaft having a keyed end for engaging with a mating keyed portion of the engaging member of the hub region of the fastener for providing the torsional force.

25. The fastener of claim 24, wherein the hub region includes at least one securement point for securing a suture thereto.

26. The fastener of claim 24, wherein the engaging member comprising at least one location adapted to receive the insertion tool for providing said rotational force.

27. The fastener of claim 25, wherein there are at least two securement points for securing a suture.

28. The fastener of claim 27, wherein the securement points comprise openings in the hub through which the suture is traversable.

29. The fastener of claim 26, wherein the engaging member comprises at least one opening adapted to receive a portion of the insertion tool.

30. The fastener of claim 24, wherein the longitudinally extending member has the shape of a flattened oval in plan view.

31. The fastener of claim 24, wherein the sharp edges have an angle from the plane of the longitudinally extending member of about 30°.

32. The fastener of claim 24, wherein each arm has two sharp edges, thereby allowing rotation to secure the fastener in two opposite rotational directions.

33. The fastener of claim 24, further comprising at least one fin or rib projecting from a surface of each arm, the fins or ribs having sharp edges.

34. The fastener of claim 33, wherein the fins or ribs project substantially perpendicularly from the surface.

35. The fastener of claim 33, wherein the fins or ribs are curved in the direction of the rotational force.

36. The fastener of claim 33, wherein the fins or ribs are disposed on a lower surface of the arms.

37. The fastener of claim 33, further comprising said insertion tool for releasably holding the fastener and providing the rotational force to secure the fastener.

38. The fastener of claim 24, wherein the fastener comprises a biocompatible material adapted to be inserted in bone.

39. The fastener of claim 25, wherein the fastener comprises a biocompatible material adapted to be inserted in bone and the suture is adapted to secure a ligament or ligament replacement to the bone.

40. The fastener of claim 24, wherein the member comprises one of a biocompatible metal, plastic or ceramic.

41. A fastening apparatus, comprising:

an insertion tool having an insertion tool axis;

a fastener including a longitudinally extending member having a hub region and at least two arms extending in a longitudinal direction from the hub region, the longitudinally extending member defining a plane and having a length and a width, the hub region defining an axis of rotation of the longitudinally extending member which is along the insertion tool;

the arms each being provided with a sharp edge;

the hub region being provided with an engaging member, the engaging member being adapted to engage the insertion tool such that the plane defined by the longitudinally extending member is perpendicular to the insertion tool axis, the engaging member being adapted to receive a torsional force about said insertion tool axis perpendicular to the plane of the longitudinally extending member for rotating the longitudinally extending member in the plane of the longitudinally extending member;

the fastener being adapted to be inserted in a longitudinally extending groove in an object to which the fastener is to be secured, the groove being at least coextensive with the length of the longitudinally extending member and having a width at least as large as the width of the longitudinally extending member, the fastener being adapted to be rotated via the torsional force from the insertion tool once inserted in the groove so that the sharp edges of the arms cut into sides of the grooves thereby forming undercuts securing the fastener in the object, and the insertion tool comprising a shaft extending along the insertion tool axis, the shaft having a keyed end for engaging with a mating keyed portion of the engaging member of the hub region of the fastener for providing the torsional force.

* * * * *